(12) United States Patent
Guo et al.

(10) Patent No.: US 8,624,049 B2
(45) Date of Patent: Jan. 7, 2014

(54) DOPANT GROUP-SUBSTITUTED SEMICONDUCTOR PRECURSOR COMPOUNDS, COMPOSITIONS CONTAINING THE SAME, AND METHODS OF MAKING SUCH COMPOUNDS AND COMPOSITIONS

(75) Inventors: Wenzhuo Guo, Cupertino, CA (US); Vladimir K. Dioumaev, Mountain View, CA (US); Brent Ridley, San Carlos, CA (US); Fabio Zürcher, Brisbane, CA (US); Joerg Rockenberger, Redwood City, CA (US); James Montague Cleeves, Redwood City, CA (US)

(73) Assignee: Kovio, Inc., San Jose, CA (US)

( * ) Notice: Subject to any disclaimer, the term of this patent is extended or adjusted under 35 U.S.C. 154(b) by 731 days.

(21) Appl. No.: 12/689,210

(22) Filed: Jan. 18, 2010

(65) Prior Publication Data

US 2011/0178321 A1    Jul. 21, 2011

(51) Int. Cl.
*C07F 7/08*    (2006.01)

(52) U.S. Cl.
USPC .......................................... 556/406; 526/279

(58) Field of Classification Search
None
See application file for complete search history.

(56) References Cited

U.S. PATENT DOCUMENTS

| | | | |
|---|---|---|---|
| 4,554,180 A | 11/1985 | Hirooka | |
| 4,683,146 A | 7/1987 | Hirai et al. | |
| 5,866,471 A | 2/1999 | Beppu et al. | |
| 6,503,570 B2 * | 1/2003 | Matsuki et al. | 427/387 |
| 6,517,911 B1 | 2/2003 | Matsuki | |
| 6,518,087 B1 | 2/2003 | Furusawa et al. | |
| 6,527,847 B1 | 3/2003 | Matsuki | |
| 6,541,354 B1 | 4/2003 | Shimoda et al. | |
| 6,593,591 B2 | 7/2003 | Yudasaka et al. | |
| 6,767,775 B1 | 7/2004 | Yudasaka et al. | |
| 7,071,125 B2 | 7/2006 | McSwiney et al. | |
| 7,314,513 B1 | 1/2008 | Zurcher et al. | |
| 7,498,015 B1 * | 3/2009 | Kunze et al. | 423/645 |
| 7,619,248 B1 * | 11/2009 | Cleeves | 257/57 |
| 7,674,926 B1 * | 3/2010 | Guo et al. | 556/404 |
| 7,981,482 B1 * | 7/2011 | Zurcher et al. | 427/510 |
| 8,211,396 B1 * | 7/2012 | Guo et al. | 423/324 |
| 8,236,916 B1 * | 8/2012 | Guo et al. | 528/31 |
| 2003/0045632 A1 | 3/2003 | Shiho et al. | |
| 2003/0148024 A1 | 8/2003 | Kodas et al. | |
| 2003/0229190 A1 | 12/2003 | Aoki et al. | |
| 2005/0176183 A1 | 8/2005 | Aoki | |
| 2006/0211187 A1 * | 9/2006 | Choi et al. | 438/197 |
| 2007/0078252 A1 * | 4/2007 | Dioumaev | 528/31 |
| 2007/0287237 A1 * | 12/2007 | Rockenberger et al. | 438/163 |
| 2008/0022897 A1 * | 1/2008 | Zurcher et al. | 106/287.14 |
| 2008/0044964 A1 * | 2/2008 | Kamath et al. | 438/164 |

FOREIGN PATENT DOCUMENTS

| | | |
|---|---|---|
| GB | 2 077 710 A | 12/1981 |
| JP | 60-242612 | 12/1985 |
| JP | 6-191821 | 7/1994 |
| JP | 7-267621 | 10/1995 |
| JP | 9-45922 | 2/1997 |
| WO | 00/59041 | 10/2000 |

OTHER PUBLICATIONS

Uwe Herzog & Robert West; "Heterosubstituted Poysilanes"; pp. 2210-2214; Macromolecules 1999, 32; American Chemical Society, Mar. 9, 1999.

* cited by examiner

*Primary Examiner* — Sudhakar Katakam

(74) *Attorney, Agent, or Firm* — Murabito, Hao & Barnes LLP; Andrew D. Fortney

(57) ABSTRACT

Dopant-group substituted (cyclo)silane compounds, liquid-phase compositions containing such compounds, and methods for making the same. Such compounds (and/or ink compositions containing the same) are useful for printing or spin coating a doped silane film onto a substrate that can easily be converted into a doped amorphous or polycrystalline silicon film suitable for electronic devices. Thus, the present invention advantageously provides commercial qualities and quantities of doped semiconductor films from a doped "liquid silicon" composition.

20 Claims, 4 Drawing Sheets

US 8,624,049 B2

DOPANT GROUP-SUBSTITUTED SEMICONDUCTOR PRECURSOR COMPOUNDS, COMPOSITIONS CONTAINING THE SAME, AND METHODS OF MAKING SUCH COMPOUNDS AND COMPOSITIONS

FIELD OF THE INVENTION

The present invention generally relates to the field of dopant group-substituted semiconductor precursor compounds, compositions containing such compounds, methods for the synthesis of such compounds, and methods of making such compositions. More specifically, embodiments of the present invention pertain to hetero-substituted (cyclo)silane compounds of the formula $(A_nH_z)_m(DR^1{}_{3-m})_q$, where A is Si and/or Ge and D is B, P, As or Sb; doped semiconductor precursor inks containing such compounds; and methods of making such compounds and ink compositions.

DISCUSSION OF THE BACKGROUND

There are a number of silanes that are liquid at ambient temperatures (e.g., from about 15° C. to about 30° C.) or that can be formulated into an ink composition that is liquid at ambient temperatures. Liquid silanes, such as cyclopentasilane or cyclohexasilane, have been investigated as candidate "liquid silicon" precursors. However, to date, it has been challenging to make semiconducting thin films of commercial qualities and quantities from "liquid silicon" precursors. One such challenge has related to doping such "liquid silicon" precursors and/or the films formed therefrom.

Methods have been proposed for covalently binding dopant atoms such as phosphorous and boron to silicon atoms in certain liquid (cyclo)silanes. For example, photochemical reactions between (cyclo)silanes and certain phosphines and/or boranes are disclosed in U.S. Pat. No. 4,683,145 and U.S. Patent Publication No. 2003/0229190. Heterocyclic doped silanes are disclosed in U.S. Pat. No. 6,527,847 and U.S. Patent Publication No. 2003/0045632, and a method for synthesizing such doped silanes is disclosed in U.S. Pat. No. 6,527,847. The properties of thin films formed from such compounds are somewhat disappointing, given the relative proportion of dopant atoms in the film-forming mixture. Also, the results are not quite as reproducible as may be generally desired for commercial applications.

The mechanisms behind the disappointing results are not well understood. However, there may be a number of critical steps involved in forming doped semiconducting films from doped liquid silanes, such as forming the covalent bonds between dopant atoms and silicon, preserving these covalent bonds during subsequent synthesis steps and in initial processing steps to form a thin film or thin film structure, and activating the dopant atoms once the thin film or thin film structure is formed.

Thus, there has been a long-felt need in the art for a "liquid silicon" compound and/or composition, particularly a doped "liquid silicon." Such a composition would primarily comprise silicon atoms (other than solvent, to the extent solvent may be present as a main component), would include a dopant or dopant precursor, would be liquid at ambient temperatures (to facilitate handling, deposition and further processing), and would yield commercial quality semiconducting films upon subsequent processing (e.g., annealing or curing). However, to date, methods of making a thin doped semiconducting film or film structure from doped liquid silanes (or liquid compositions comprising doped silanes) have not been sufficiently reliable for high-volume commercial use.

SUMMARY OF THE INVENTION

Embodiments of the present invention relate to novel dopant group-substituted (cyclo)silane compounds, to compositions containing such compounds, and to methods of synthesizing such compounds and formulating such compositions. The compounds and compositions are generally useful for making (e.g., by printing or spin-coating, then curing and/or annealing) doped semiconductor thin films (see, e.g., copending U.S. application Ser. No. 10/949,013, filed Sep. 24, 2004). Thus, the present invention advantageously provides a means for obtaining commercial qualities and quantities of thin doped semiconductor films from a "doped liquid silicon" composition.

The present invention relates to compounds of the formula $(A_nH_z)_m(DR^1{}_{3-m})_q$, where n is an integer from 3 to 12, z is from (n−q) to (2n+2−q), m is an integer from 1 to 3, each of the n*m instances of A is independently Si or Ge, D is Sb, As, P or B, q is generally 1 or 2, and each of the (3−m)*q instances of $R^1$ is independently H, alkyl, aryl, aralkyl, or $AR^2{}_3$, where $R^2$ is hydrogen, alkyl, aryl, aralkyl, or $A_pH_{2p+1}$ (1≤p≤4). However, none of the covalent A-D bonds in the present compound is in a cyclic ring; hence, the characterization of the present compounds as "dopant group-substituted." Furthermore, when m=1 and $A_nH_z$ is a straight-chain, non-cyclic group of the formula n-$A_nH_{2n+2-q}$, then at most one of the (3−m) instances of $R^1$ is H. The present composition generally comprises the present hetero-substituted (cyclo)silane and a solvent in which the hetero-substituted (cyclo)silane is soluble.

The present invention further relates to methods for synthesizing such compounds, generally comprising (a) reacting a (cyclo)silane of the formula $A_nH_y$ (where y is an even integer of from n to 2n+2) with a dopant group precursor of the formula $DR^1{}_3$ or $DR^1{}_{3-m}X_m$ to form a dopant group-substituted (cyclo)silane compound; and (b) purifying and/or isolating the dopant group-substituted (cyclo)silane compound. The method of making the composition generally comprises combining the hetero-substituted (cyclo)silane with a solvent, and mixing the hetero-substituted (cyclo)silane and the solvent sufficiently to dissolve the hetero-substituted (cyclo)silane in the solvent.

These and other advantages of the present invention will become readily apparent from the detailed description of preferred embodiments below.

DETAILED DESCRIPTION OF THE PREFERRED EMBODIMENTS

Figure 1A:
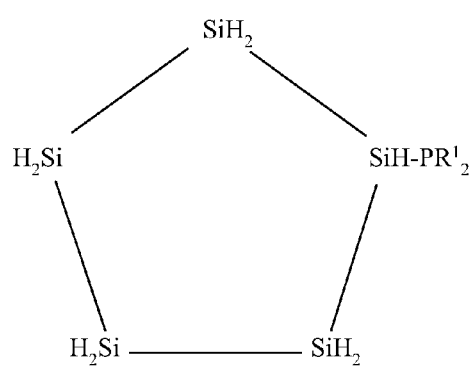
FIGS. 1A-1I show representative dopant group-substituted (cyclo)silanes in accordance with the present invention.

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be readily apparent to one skilled in the art that the present invention may be practiced without these specific details. In other instances, well-known methods, procedures, components, and circuits have not been described in detail so as not to unnecessarily obscure aspects of the present invention.

For the sake of convenience and simplicity, the terms "$C_a$-$C_b$ alkyl," "$C_a$-$C_b$ alkoxy," etc., shall refer to both branched and unbranched moieties, to the extent the range from a to b covers 3 or more carbon atoms. Unless otherwise indicated, the terms "arene," "aryl," and "ar-" refer to both mono- and polycyclic aromatic species, to the extent possible and/or applicable. The terms "silane" and "(cyclo)silane" may be used interchangeably herein, and unless expressly indicated otherwise, these terms refer to compounds or mixtures of compounds that consist essentially of (1) silicon and/or germanium and (2) hydrogen. The terms "hetero-substituted" and "dopant group-substituted" may be used interchangeably herein, and unless expressly indicated otherwise, these terms refer to groups containing a dopant atom such as B, P, As or Sb having a covalent bond to, but that is not part of a cyclic species with, one or more semiconductor element atoms (e.g., silicon and/or germanium). The prefix "(cyclo)-" generally refers to a compound or mixture of compounds that may contain a cyclic ring, and the prefix "cyclo-" generally refers to a compound or mixture of compounds that contain one or more cyclic rings. The terms "halo-," "halide" and grammatical variations thereof generally refer to halogens as defined in the Periodic Table of Elements (e.g., F, Cl, Br, and I) and halogen-like species (e.g., that form stable monovalent anions) such as methanesulfonate (OMs), trifluoromethanesulfonate (OTf), benzylsulfonate (OBz), toluenesulfonate (OTs), etc. Also, the terms "isolating" and "purifying" (and grammatical variations thereof) may be used interchangeably herein, but these terms are intended to have their art-recognized meanings, unless expressly indicated otherwise.

The present invention concerns a hetero-substituted (cyclo)silane compound of the formula $(A_nH_z)_m(DR^1_{3-m})_q$, compositions containing the same, and methods of making the same. In the present hetero-substituted (cyclo)silane compound, n is generally from 3 to 12, z is from (n-q) to (2n+2-q), m is an integer of from 1 to 3, each of the n instances of A is independently Si or Ge, q is generally 1 or 2, each of the q instances of D is P, As, Sb or B, and each of the q*(3-m) instances of $R^1$ is independently H, alkyl, aryl, aralkyl or $AR^2_3$, where $R^2$ is hydrogen, alkyl, aryl, aralkyl, or $A_pH_{2p+1}$ (where p is from 1 to 4; e.g., $SiH_3$); such that none of the covalent A-D bonds in the formula is in a cyclic ring, and when m=1 and $A_nH_z$ is a linear or branched group of the formula n-$A_nH_{2n+2-q}$, then at most one of the (3-m) instances of $R^1$ is H.

The method of making dopant group-substituted (cyclo)silanes generally comprises the steps of: (a) reacting a (cyclo)silane of the formula $A_nH_y$ (where y is an even integer of from n to 2n+2) with a dopant group precursor of the formula $DR^1_3$ or $DR^1_{3-m}X_m$ to form a dopant group-substituted (cyclo)silane compound; and (b) purifying and/or isolating the dopant group-substituted (cyclo)silane compound. In one embodiment, the (cyclo)silane is photoreacted with a dopant group precursor of the formula $DR^1_3$ to form a dopant group-substituted (cyclo)silane compound of the formula $(A_nH_z)(DR^1_2)_q$, where z=y-q. In another embodiment, a (cyclo)silane of the formula $A_nH_y$ (where y is an even integer of from n to 2n+2) is reduced with an alkali metal, then reacted with dopant group precursor of the formula $DR^1_{3-m}X_m$ to form the dopant group-substituted (cyclo)silane, the structure of which depends on the identity of the alkali metal (and, to some extent, on whether the silane is cyclic or not). For example, when the alkali metal is Li, one may react two mole equivalents of the alkali metal and a dopant group precursor of the formula $DR^1_2X$ with one mole equivalent of a cyclosilane to form a dopant group-substituted silane of the formula $R^1_2D$-$(A_nH_y)$-$DR^1_2$. Alternatively, one may make a heterocyclosilane of the formula $A_nH_yDR^1$ by reacting two mole equivalents of Li metal with one mole equivalent of a cyclosilane, then one mole equivalent of a dopant group precursor of the formula $DR^1X_2$. On the other hand, when the alkali metal is not Li, one may react m mole equivalents of the alkali metal and the (cyclo)silane with a dopant group precursor of the formula $DR^1_{3-m}X_m$ to form a dopant group-substituted (cyclo)silane of the formula

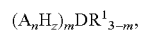

where z=y-1.

The composition generally comprises the present hetero-substituted (cyclo)silane and a solvent in which the hetero-substituted (cyclo)silane is soluble. The method of making the composition generally comprises combining the hetero-substituted (cyclo)silane with a solvent, and mixing the hetero-substituted (cyclo)silane and the solvent sufficiently to dissolve the hetero-substituted (cyclo)silane in the solvent.

The invention, in its various aspects, will be explained in greater detail below with regard to exemplary embodiments.

Exemplary Hetero-Substituted (Cyclo)Silane Compounds

The present invention relates to a hetero-substituted (cyclo)silane compound of the formula $(A_nH_z)_m(DR^1_{3-m})_q$, where n is from 3 to 12, z is from (n-q) to (2n+2-q), m is from 1 to 3, each of the n instances of A is independently Si or Ge, D is Sb, As, P or B, q is generally 1 or 2, and each of the (3-m) instances of $R^1$ is independently H, alkyl, aryl, aralkyl, or $AR^2_3$, where $R^2$ is hydrogen, alkyl, aryl, aralkyl, or $A_pH_{2p+1}$ (e.g., 1≤p≤4). Generally, each of the covalent A-D bonds in the present hetero-substituted (cyclo)silane is not in a cyclic ring. In certain preferred embodiments of this compound, A is Si, n is 4 to 6 (predominantly 5), $(A_nH_z)$ is monocyclic (i.e., z is 2n-q), m and q are each 1, and/or $R^1$ is $C_1$-$C_6$ alkyl (e.g., t-butyl), $C_6$-$C_{12}$ aryl (e.g., phenyl), $C_7$-$C_{12}$ aralkyl (e.g., benzyl, α,α-dimethylbenzyl), $SiH_3$, or $Si(SiH_3)_3$, although other embodiments may be preferred under certain circumstances. For example, in one embodiment, m is 1, and for each of the q instances of $DR^1_2$, one $R^1$ may be H and the remaining instances selected from $C_1$-$C_6$ alkyl, $C_6$-$C_{12}$ aryl, $SiH_3$, and $Si(SiH_3)_3$. In embodiments where m=3, generally q=1.

The present invention relates in part to hetero-substituted cyclosilane compounds of the formula $(A_nH_z)_mDR^1_{3-m}$, where n is from 3 to 12, z is an odd number from (n-1) to (2n-1) (preferably [y-1]), m is from 1 to 3, each of the n instances of A is independently Si or Ge, D is Sb, As, P or B, and each of the (3-m) instances of $R^1$ is H, alkyl, aryl, aralkyl, or $AR^2_3$, where $R^2$ is hydrogen, alkyl, aryl, aralkyl, or $A_pH_{2p+1}$ (where p is an integer of 1 to 4). In certain preferred embodiments, A is Si, n is 4 to 6 (preferably 5), z is (2n-1), D is P or B, and/or m is 1, although other embodiments may be preferred under certain circumstances.

For example, one or more of the n instances of A may be Ge, in which case the present hetero-substituted (cyclo)silane compounds may comprise a substituted silagermane compound having the formula $(Si_{n-i}Ge_iH_z)_m DR^1_{3-m}$, where i is an integer of at least 1 but less than n. Depending on the choice of starting materials (see, e.g., U.S. patent application Ser. No. 10/789,317, filed Feb. 27, 2004, the relevant portions of which are incorporated herein by reference), the present compounds may be formed from a somewhat statistical mixture of cyclosilane compounds and cyclosilagermane compounds (e.g., in which there is a statistical distribution of compounds with specific n and i values).

Figure 1B:
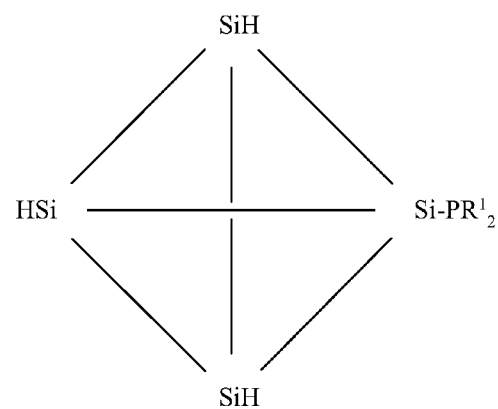
Figure 1C:
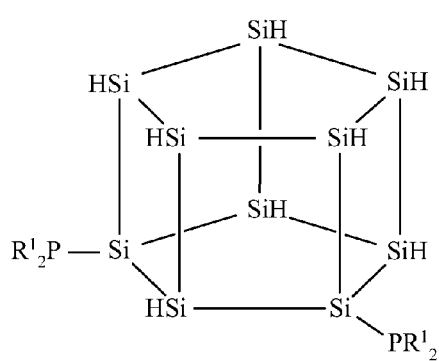

FIGS. 1A-1F show various hetero-substituted cyclosilane compounds in which A is Si, D is P, and $4 \leq n \leq 12$, but as is understood by those skilled in the art, essentially any Si atom in any of these compounds can be replaced by Ge, and any P atom in any of these compounds can be replaced by B, As or Sb. FIG. 1A shows a preferred dopant group-substituted cyclosilane, in which n=5 and z=2n−1. FIG. 1B shows a dopant group-substituted cyclosilane, in which n=4 and z=n−1. FIG. 1C shows such a hetero-substituted polycyclosilane compound in which both n=10, m=1, and q=2. Also as shown in the compound of FIG. 1C, when q is 2 and the formula $A_nH_z$ contains a polycyclosilyl moiety, the two $DR^1_{3-m}$ groups may be covalently bound to A atoms that are members of a common ring. Positional and stereochemical isomers of the present compounds (such as isomers of the compound of FIG. 1C) are also encompassed by the present invention. Furthermore, as is explained in greater detail below with regard to a "photochemical coupling" embodiment of the present method of making dopant group-substituted (cyclo)silanes, q can be greater than 2. In theory, up to all y H atoms in the (cyclo)silane can be replaced with -$DR^1_2$ groups; however, due to steric crowding and/or hindrance effects, q is generally expected to be not greater than n when the silane is cyclic, and not greater than (n+2) when the silane is not cyclic.

Figure 1D:
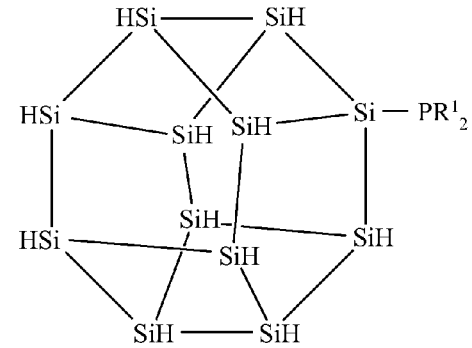
Figure 1E:
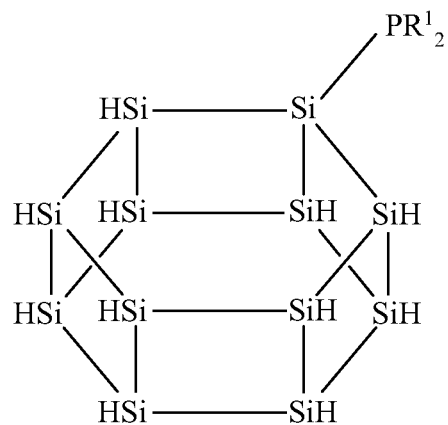
Figure 1F:
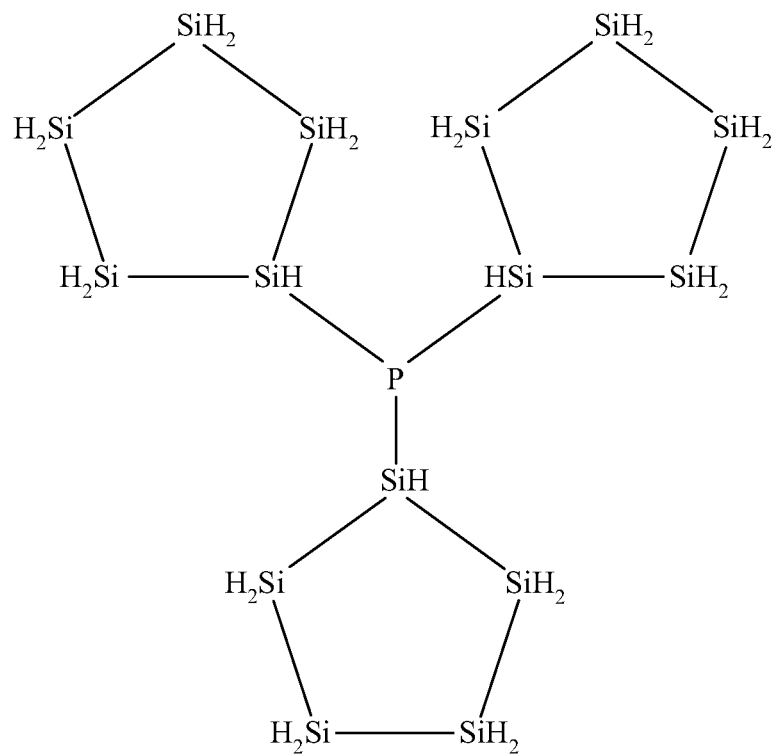
Figure 1G:
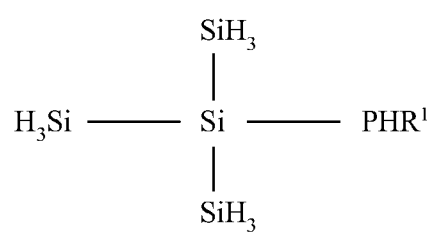
Figure 1H:
Figure 1I:
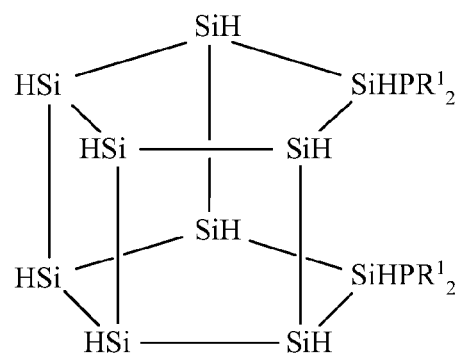

FIGS. 1D and 1E show two different structures for a hetero-substituted polycyclosilane compound in which n=12 and z=n−1. FIG. 1F shows a dopant atom-substituted cyclosilane in which n=5, z=2n−1, and m=3, that can be synthesized according to the "Na/K" embodiment of the present method of making dopant group-substituted (cyclo)silanes disclosed below. FIG. 1G shows a heterosilane compound in which n=4, m=1 and one of the $R^1$ groups is H that may be made using either the photochemical coupling or the Na/K embodiment of the present method of making dopant group-substituted (cyclo)silanes. FIGS. 1H and 1I respectively show hetero-substituted silane and hetero-substituted cyclosilane compounds in which m=1, q=2, and n=5 or 10, that are synthesized using the "Li" embodiment of the present method of making dopant group-substituted (cyclo)silanes disclosed below.

Generally, when $n \leq 6$, the present hetero-substituted cyclosilane compounds are monocyclic (see FIGS. 1A and 1F); when $n \geq 8$, the present hetero-substituted cyclosilane compounds are generally polycyclic (see FIGS. 1C-1E and 1I); and when $6 \leq n \leq 8$, the present hetero-substituted cyclosilane compounds may be monocyclic or polycyclic. Thus, in some preferred embodiments, $4 \leq n \leq 10$; more preferably, $4 \leq n \leq 6$; and in one preferred compound, n is 5.

One distinguishing feature of certain hetero-substituted (cyclo)silane compounds is the $R^1$ group covalently bound to the dopant atom D. For example, $R^1$ may be $C_1$-$C_6$ alkyl (e.g., methyl, ethyl, propyl, isopropyl, n-butyl, t-butyl, n-hexyl or t-hexyl [1,1-dimethylbutyl]), $C_6$-$C_{12}$ aryl (e.g., phenyl, α- or β-naphthyl, tolyl [o-, m- or p-methylphenyl], xylyl [e.g., 1,4-dimethylphenyl], cymyl [o-, m- or p-methylisopropylphenyl], t-butylphenyl, etc.), $C_7$-$C_{12}$ aralkyl (e.g., benzyl, 1,5-dimethylbenzyl, α,α-dimethylbenzyl, etc.), $SiH_3$, or $Si(SiH_3)_3$ (i.e., y=1), although when $R^1$ is $AR^2_3$, $R^2$ can be hydrogen, $C_1$-$C_6$ alkyl, $C_6$-$C_{12}$ aryl or $C_7$-$C_{12}$ aralkyl as described above. In certain implementations, $R^1$ is t-butyl or phenyl. In other implementations, $R^1$ is $SiH_3$ or $Si(SiH_3)_3$.

In theory, dopant atom D may be any conventional dopant atom used in the semiconductor field. In practice, however, D is generally P, As, Sb or B (preferably P or B). One characteristic of a thin semiconducting film made from the present hetero-substituted (cyclo)silane compounds is that the dopant is uniformly distributed throughout the thin film (see, e.g., copending U.S. application Ser. No. 10/949,013, filed Sep. 24, 2004, the relevant portions of which are incorporated herein by reference). Surprisingly, the presence of a carbon-containing substituent on the dopant atom does not result in a significant increase in the amount of carbon in doped semiconductor films formed from the present hetero-substituted (cyclo)silane compounds, or in significant adverse effects on the physical and/or structural properties of such films, relative to undoped films formed from structurally analogous cyclosilanes (e.g., cyclopentasilane).

In an alternative embodiment, the present compound comprises a hetero-substituted silane compound of the formula $(A_nH_y)(DR^1_2)_2$, where n and y are as defined above, each of the n instances of A is independently Si or Ge, D is Sb, As, P or B, and each $R^1$ is independently H, alkyl, aryl, aralkyl, or $AR^2_3$, where $R^2$ is hydrogen, alkyl, aryl, aralkyl, or $A_pH_{2p+1}$ (e.g., $1 \leq p \leq 4$). In certain preferred embodiments of this compound, the formula is $(AH_2)_n(DR^1_2)_2$, A is Si, n is 4 to 6 (and predominantly 5), and $R^1$ is $C_1$-$C_6$ alkyl (e.g., t-butyl), $C_6$-$C_{12}$ aryl (e.g., phenyl), $C_7$-$C_{12}$ aralkyl, $SiH_3$, or $Si(SiH_3)_3$, although other embodiments may be preferred under certain circumstances. One example of this type of compound is shown in FIG. 1H, where n=5, m=1, and q=2.

Exemplary Hetero-Substituted (Cyclo)Silane Compositions and Methods of Making the Same The invention further relates to a composition comprising the present hetero-substituted (cyclo)silane compound(s) (i.e., of the formula $(A_nH_z)_m(DR^1_{3-m})_q$) and a solvent in which the hetero-substituted (cyclo)silane is soluble. Thus, preferred compositions include those that contain one or more preferred hetero-substituted (cyclo)silanes compound (e.g., where A is Si, z is 2n−q, n is 4-6, m is 1, D is P or B, and/or $R^1$ is $C_1$-$C_6$ alkyl, $C_6$-$C_{12}$ aryl, $C_7$-$C_{12}$ aralkyl, $SiH_3$, or $Si(SiH_3)_3$ [particularly where $R^1$ is t-butyl or phenyl]).

The solvent in the present composition is one that is generally easily and/or thoroughly removable from the composition. Thus, in one embodiment, the solvent is selected from the group consisting of alkanes, substituted alkanes, cycloalkanes, substituted cycloalkanes, arenes, substituted arenes, and (cyclic) siloxanes, preferably those having a boiling point at 1 atm pressure of <250° C., ≤200° C., or ≤150° C.

While other apolar and/or non-polar solvents (e.g., saturated hydrocarbons such as $C_5$-$C_{12}$ alkanes, aliphatic ethers such as di-$C_2$-$C_6$ alkyl ethers, methyl $C_4$-$C_6$ alkyl ethers and di-$C_1$-$C_4$ alkyl $C_2$-$C_6$ alkylene diethers [e.g., glyme], cyclic ethers such as tetrahydrofuran and dioxane, (cyclo)siloxanes, arenes such as benzene, toluene and xylenes, etc.) may be included in the present composition, mono- or polycycloalkanes, (cyclic) siloxanes and fluoroalkanes are generally preferred for their removability from the composition. Somewhat surprisingly, mono- and bicycloalkanes (e.g., monocyclooctane, decalin) provide ink formulations with improved stability relative to aromatic hydrocarbon solvents. Furthermore, the (doped) (cyclo)silanes are generally more soluble in mono- or bicycloalkane solvents than in arene-based solvents.

Thus, the solvent may be selected from the group consisting of $C_5$-$C_{12}$ or $C_6$-$C_{10}$ alkanes; $C_1$-$C_6$ alkanes substituted with from 1 to 2n halogen (e.g., 1 to 4 chlorine substituents) or from 1 to n (e.g., 1 or 2) $C_1$-$C_4$ alkoxy substituents; $C_5$-$C_{12}$ monocycloalkanes; $C_3$-$C_8$ monocycloalkanes substituted with from 1 to 2n $C_1$-$C_4$ alkyl or halogen substituents (e.g., 1 or 2 $C_1$-$C_4$ alkyl or chlorine substituents, or 2n fluorine substituents) or from 1 to n $C_1$-$C_4$ alkoxy substituents (e.g., 1 $C_1$-$C_4$ alkoxy substituent), where n is the number of carbon atoms in the monocycloalkane ring; $C_{10}$-$C_{14}$ polycycloalkanes and partially hydrogenated polycycloarenes (e.g., decalin, tetralin); siloxanes of the formula $(R^4_3Si)(OSiR^4_2)_r(OSiR^4_3)$ and cyclosiloxanes of the formula $(SiR^4_2O)_q$, where r is from 0 to 4, q is from 2 to 6 (preferably from 3 to 5), each $R^4$ is independently H, $C_1$-$C_6$ alkyl, benzyl or phenyl substituted with from 0 to 3 $C_1$-$C_4$ alkyl groups (preferably each $R^4$ is methyl); and $C_3$-$C_8$ fluoroalkanes substituted with from 1 to (2t+2) fluorine atoms and that are liquid at ambient temperatures, where t is the number of carbon atoms in the fluoroalkane. The (cyclo)siloxane solvents are generally those that are liquid at ambient temperatures (e.g., 15-30° C.). Preferably, the solvent is a $C_5$-$C_{12}$ mono- or bicycloalkane (e.g., cyclopentane, cyclohexane, cycloheptane, cyclooctane, decalin, etc.).

The composition may contain from 0.00001 to 50 vol %, from 0.0001 to 35 vol %, or from about 0.001 to 25 vol % of the hetero-substituted (cyclo)silane compound. Conversely, from 0.00001 to 50 vol %, from 0.0001 to 35 vol %, or from about 0.0001 to 25 vol % of the composition may comprise or consist essentially of the hetero-substituted (cyclo)silane compound. Alternatively, the composition may further contain a (cyclo)silane and a sufficient percentage (by volume, mass/weight or atoms) of the dopant group-substituted (cyclo)silane compound to result in a semiconductor film having from $10^{16}$ to $10^{21}$ atoms/cm$^3$ of dopant therein (see, e.g., copending U.S. application Ser. No. 10/950,373, filed Sep. 24, 2004, the relevant portions of which are incorporated herein by reference). Thus, proportions (in vol. %) of hetero-substituted (cyclo)silane and (cyclo)silane components in ink formulations may be selected such that the semiconductor film has a predetermined level of doping (in atoms/cm$^3$).

The composition may further comprise one or more conventional additives, such as a surface tension reducing agent, a surfactant, a binder and/or a thickening agent, generally in conventional amount(s) (e.g., from 0.001 to 10 wt. %). However, such additives are not at all necessary. As a result, the present composition may consist essentially of the hetero-substituted (cyclo)silane compound, one or more (cyclo)silane compounds (e.g., as discussed immediately below), and the solvent. Alternatively, the present composition may consist essentially of the hetero-substituted (cyclo)silane (optionally with one or more [cyclo]silane compounds), without the addition of a solvent (in which case, when present, the [cyclo]silane compound[s] may be the solvent).

The composition may also further contain a (cyclo)silane compound of the formula $A'_kH_j$, where k is from 3 to 20, j is from k to (2k+2), and each A' is independently Si or Ge. In a preferred embodiment, the composition further contains a cyclosilane compound of the formula $(A'H_x)_k$, where k is from 3 to 12, each of the k instances of x is 1 or 2, and each A' is independently Si or Ge (see, e.g., U.S. patent application Ser. No. 10/789,317, filed Feb. 27, 2004, the relevant portions of which are incorporated herein by reference). Typically, in various preferred cyclosilanes, A is Si, x is 2, and/or k is from 4 to 6. In further embodiments of the present composition, from 0.1 to 50 vol %, from 0.5 to 35 vol %, or from about 1 to 25 vol % of the composition consists essentially of the cyclosilane compound. Alternatively, from about 1 to 100 vol %, from 5 to 50 vol %, or from 10 to 35 vol % of the composition consists essentially of the hetero-substituted (cyclo)silane compound and the cyclosilane compound. In this alternative embodiment, the volume ratio of hetero-substituted (cyclo)silane compound to cyclosilane compound may be from about 1:100,000 to about 1:1. Thus, in one embodiment, the cyclosilane compound can serve as the solvent in the composition (at least when the cyclosilane compound is liquid at ambient temperatures).

The present invention further relates to a method of making the present composition, comprising the steps of combining the hetero-substituted (cyclo)silane compound with a solvent (and, optionally, with a [cyclo]silane); and mixing the hetero-substituted (cyclo)silane compound and the solvent (and optional [cyclo]silane) to form a solution of the hetero-substituted (cyclo)silane (and optional [cyclo]silane) in the solvent. The solvent can be any of those mentioned above, but in preferred embodiments, the solvent consists essentially of a member selected from the group consisting of $C_5$-$C_{12}$ mono- or polycycloalkanes; $C_3$-$C_{10}$ mono- or polycycloalkanes substituted with from 1 to 2n $C_1$-$C_4$ alkyl or halogen substituents or from 1 to n $C_1$-$C_4$ alkoxy substituents, where n is the number of carbon atoms in the cycloalkane ring; and $C_3$-$C_8$ fluoroalkanes substituted with from 1 to (2t+2) fluorine atoms and that are liquid at ambient temperatures, where t is the number of carbon atoms in the fluoroalkane. Most preferably, the solvent consists essentially of a $C_5$-$C_{10}$ mono- or bicycloalkane (e.g., cyclooctane, decalin, etc.).

The method may further comprise combining a surface tension reducing agent, a surfactant, a binder, a thickening agent and/or the (cyclo)silane compound of the formula $A'_kH_j$ described herein, with or without the solvent, generally in an amount as described herein. In one implementation, the composition may be prepared by mixing about 10-25 vol. % of the hetero-substituted (cyclo)silane (alone or in combination with an undoped [cyclo]silane) with cyclooctane under an inert (e.g., argon) atmosphere. In one variation, the mixture may be stored in amber vials to prevent exposure to UV or other radiation. The composition consisting of liquid-phase components may be used directly to (i) coat a substrate with a thin doped silane film and/or (ii) form or print a doped silane and/or semiconductor thin film on a substrate.

Exemplary Methods of Making Hetero-substituted (Cyclo)silane Compounds

A further aspect of the present invention relates to a method of making a dopant group-substituted (cyclo)silane, comprising the steps of (a) reacting a (cyclo)silane of the formula $A_nH_y$ with a dopant group precursor of the formula $DR^1_3$ or $DR^1_{3-m}X_m$ to form a dopant group-substituted (cyclo)silane, where n is an integer from 3 to 12, m is an integer from 1 to 3, each of the n instances of A is independently Si or Ge, y is an even integer of from n to (2n+2), D is Sb, As, P or B, each of the (3−m) instances of $R^1$ is independently H, alkyl, aryl, aralkyl, or $AR^2_3$ (where $R^2$ is hydrogen, alkyl, aryl, aralkyl, or $A_pH_{2p+1}$, 1≤p≤4), and each of the instances of X is independently a halogen; and (b) purifying and/or isolating the dopant group-substituted (cyclo)silane. In certain preferred embodiments of this method, A is Si, n is an integer of from 4 to 6 (preferably predominantly 5), m is 1 and/or D is P or B, although other embodiments may be preferred under certain circumstances. Exemplary techniques for purifying and/or isolating the dopant group-substituted (cyclo)silane are described below.

Certain embodiments of this aspect of the invention may be similarly distinguished by the presence of a hydrocarbon, silyl or germyl substituent on the dopant atom D. Thus, in preferred embodiments, $R^1$ is $C_1$-$C_6$ or $C_1$-$C_4$ alkyl (e.g., t-butyl), $C_6$-$C_{12}$ or $C_6$-$C_{10}$ aryl (e.g., phenyl), $C_7$-$C_{12}$ aralkyl, $SiH_3$, or $Si(SiH_3)_3$. In specific implementations, $R^1$ may be t-butyl, phenyl, $SiH_3$, or $Si(SiH_3)_3$.

Preferred compounds of the formula $A_nH_y$ include cyclosilanes of the formula $A_nH_{2n}$ and $A_nH_n$. Cyclosilanes of the formula $A_nH_{2n}$ and preferred methods for their preparation are disclosed in copending U.S. application Ser. No. 10/789,317, filed on Feb. 27, 2004 (the relevant portions of which are incorporated herein by reference). Such cyclosilanes and methods for their synthesis are known (see, e.g., U.S. Pat. Nos. 4,554,180, 4,683,145, 4,820,788, 5,942,637, 6,503,570, and 6,527,847, and Kumada, J. Organomet. Chem., 100 (1975) 127-138, Ishikawa et al., Chem. Commun., (1969) 567, Hengge et al., J. Organomet. Chem., 212 (1981) 155-161, Hengge et al., Z. Anorg. Allg. Chem., 459 (1979) 123-130, and Hengge et al., Monatshefte für Chem., 106 (1975) 503-512, the relevant portions of which are incorporated herein by reference). The methods disclosed in any one of these references may be modified as suggested and/or disclosed in another of these references to arrive at a suitable cyclosilane. However, the preferred method comprises oligomerizing and cyclizing $ARX_3$ and/or $AR_2X_2$ (where R is, e.g., phenyl and X is, e.g., Cl), followed by treating the oligomerized and cyclized intermediate with a mixture of a Lewis acid and either a hydrogen halide or $R^3(C=O)X^1$, such as $AlCl_3$ and either HCl gas or $CH_3(C=O)Cl$, to form a corresponding halocyclosilane compound, then reducing the halocyclosilane with a metal hydride (such as lithium aluminum hydride) to form a mixture of mainly c-$(AH_2)_n$ when the starting monosilane is $AR_2X_2$ (where n is typically from 4 to 6, and is predominantly 5), and mainly polycyclo-$(AH)_n$ when the starting monosilane is $ARX_3$ (where n is typically an even integer of from 8 to 12).

Dopant group-substituted cyclosilanes in which m is 1 may be prepared by photochemical exchange of a (cyclo)silane of the formula $A_nH_y$ with a dopant group precursor of the formula $DR^1_3$ to form a compound of the formula $(A_nH_z)(DR^1_2)_q$, where z=y-q. Dopant group-substituted cyclosilanes of the formula $(A_nH_z)_mDR^1_{3-m}$, in which z=(y-1) and m is 1, 2 or 3 may be prepared by alkali metal (e.g., Na or K)-induced cleavage of a Si—H bond in a (cyclo)silane of the formula $A_nH_y$, followed by quenching with 1/m mole-equivalents of a heteroatom compound of the formula $DR^1_{3-m}X_m$, where X is a halogen (e.g., Cl). Dopant group-substituted silanes in which q is 2 and z=y (e.g., compounds of the formula $(A_nH_y)(DR^1_2)_2$) may be prepared by alkali metal (e.g., Li)-induced cleavage of a Si—Si bond in a cyclosilane of the formula $A_nH_y$ (e.g., $(AH_2)_n$), followed by quenching with 2 mole-equivalents of a heteroatom compound of the formula $DR^1_2X$, where X is a halogen (e.g., Cl). Finally, heterocyclosilanes of the formula $A_nH_yDR^1$ may be prepared by Li-induced cleavage of a Si—Si bond in a cyclosilane of the formula $A_nH_y$, followed by quenching with 1 mole-equivalent of a heteroatom compound of the formula $DR^1X_2$, where X is a halogen. Each of these approaches to synthesizing (cyclo)silanes having one or more covalently-bound dopant groups will be discussed in greater detail below.

A First Exemplary Method for Synthesizing Dopant Group-Substituted Cyclosilanes

In a first embodiment, the reacting step in the present method comprises irradiating a reaction mixture comprising a (cyclo)silane of the formula $A_nH_y$, where y is an even integer of from n to (2n+2), and a dopant group precursor of the formula $DR^1_3$. Thus, this embodiment of the general method of synthesizing dopant group-substituted (cyclo)silanes may be referred to as the "photochemical coupling" embodiment. In this embodiment, the dopant group-substituted (cyclo)silane compound formed generally has the formula $(A_nH_z)DR^1_2$, where z=(y-1), but as will be discussed below, certain dopant group-substituted (cyclo)silane compounds may have the formula $(A_nH_{y-2})(DR^1_2)_2$ (i.e., q=2).

Preferred dopant group precursors of the formula $DR^1_3$ include alkyl boranes (e.g., t-hexylborane, 2,2,4-trimethylpentylborane), aryl boranes (e.g., phenylborane), dialkyl boranes (e.g., di-t-butylborane, diisoamylborane), bicycloalkyl boranes (e.g., 9-borabicyclo[3.3.1]-nonane), diaryl boranes (e.g., diphenylborane), trialkyl boranes (e.g., trimethyl borane, triethyl borane, triisopropyl borane), triaryl boranes (e.g., triphenyl borane), alkyl phosphines (e.g., methylphosphine, ethylphosphine, n- and/or t-butylphosphine, etc.), aryl phosphines (e.g., phenylphosphine), dialkyl phosphines (e.g., dimethylphosphine, diethylphosphine, di-t-butylphosphine), diaryl phosphines (e.g., diphenylphosphine), trialkyl phosphines (e.g., trimethylphosphine, triethylphosphine, triisopropylphosphine, tri-t-butylphosphine), triaryl phosphines (e.g., triphenylphosphine), mixed alkyl-aryl phosphines (e.g., dimethylphenylphosphine, ethyldiphenylphosphine, t-butylphenylphosphine, etc.), and the arsine and stibine analogs of such phosphines. Naturally, the (di)alkyl and (di)aryl boranes may be in the form of dimers; e.g., $(R^1_2D[\mu-H])_2$. As a result, the formula $DR^1_3$ also refers to and/or includes dimers of the formulas $(R^1_2D[\mu-H])_2$ and $(R^1HD[\mu-H])_2$. It is also feasible for certain unsubstituted dopant group precursors, such as phosphine ($PH_3$), diborane ($B_2H_6$), or other boranes (such as $B_5H_9$, $B_6H_{10}$, $B_6H_{12}$, $B_9H_{15}$, $B_{10}H_{14}$, etc.) to provide a source of dopant atoms in the present photochemically synthesized hetero-substituted (cyclo)silanes.

Reaction conditions for the photochemical coupling embodiment are generally those conditions enabling the light-initiated substituent exchange reaction between $A_nH_y$ and q mole-equivalents of $DR^1_3$ to form $(A_nH_{y-q})(DR^1_2)_q$ and q mole-equivalents of $H—R^1$. Generally, the light comprises ultraviolet light (UV radiation), preferably having a wavelength absorbed by and/or sufficient to electronically excite the (cyclo)silane. In various embodiments, such radiation includes light having a wavelength within the range of from 200 nm to 440 nm, 220 nm to 400 nm, or 250 to 380 nm. A suitable source of such radiation may comprise a mercury vapor and/or arc lamp. The power output of the preferred UV lamp may be adjusted to about 0.1-20, 0.25-10 or 0.5-5 milliwatt/$cm^2$. The photochemical coupling reaction may be conducted for a length of time of from 5 minutes to 24 hours, 15 minutes to 12 hours, or 30 minutes to 8 hours, depending on the scale of the reaction and/or the concentration(s) of the reactant(s). Generally, the higher the power output, the shorter the irradiation/reaction time. The reaction vessel will generally have at least one window, wall or surface that is transparent to such radiation. Typically, such a window, wall or surface (or the entire reaction vessel) comprises quartz. The photochemical coupling reaction is generally conducted at a temperature as close to ambient as the reaction conditions allow; for example, the reaction vessel and/or the radiation source may be conventionally cooled using a water jacket (which may use recirculating ice water), ice bath, or other conventional reaction cooling means.

The solvent may be any relatively non-polar, non-reactive solvent used in photochemical coupling reactions (e.g., having a negligible absorption at the wavelength chosen for irradiation). Preferably, the solvent comprises or consists essentially of one or more alkanes (e.g., a $C_5$-$C_{12}$ or $C_6$-$C_{10}$ alkane), cycloalkanes (e.g., a $C_5$-$C_{10}$ cycloalkane), fluorinated alkanes (e.g., $C_3$-$C_8$ alkanes having from 1 to 2n+2 fluorine substituents and $C_3$-$C_6$ cycloalkanes having from 1 to 2n fluorine substituents, where n is the number of carbon atoms), arenes (e.g., benzene), substituted arenes (e.g., toluene, xylenes, etc.), aliphatic ethers (e.g., di-$C_2$-$C_6$ alkyl ethers, methyl $C_4$-$C_6$ alkyl ethers and di-$C_1$-$C_4$ alkyl $C_2$-$C_6$ alkylene diethers [e.g., glyme]), and/or cyclic ethers (such as tetrahydrofuran and dioxane).

Figure 2:
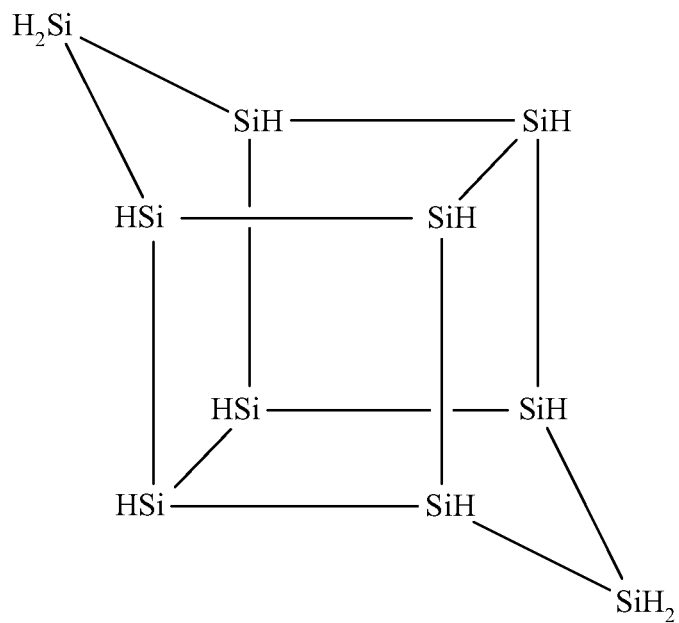
FIG. 2 shows a representative cyclosilane starting material for use in certain embodiments of the present method of synthesizing a dopant group-substituted (cyclo)silane.

Under certain conditions, certain silanes (e.g., the polycyclosilane compound of FIG. 2) may react with two (or more) mole equivalents of dopant group precursor to form a dopant group-substituted (cyclo)silane of the formula $(A_nH_{y-q})(DR^1_2)_q$, where q is an integer of 2 or more (in theory, up to y). Generally, a somewhat statistical distribution of products is expected when using two mole equivalents of dopant group precursor, in which products having q=2 will be formed in the largest percentage or proportion, products having q=1 and q=3 will be formed in the next largest (but significantly smaller) percentages or proportions, and products having q=4 may be formed in some detectable and/or isolatable amount, but other products having q≠0 may not be isolated or detected (although some amount of starting silane may be recovered). Similarly, products in which q=2 will generally be formed in a detectable and/or isolatable amount in the photochemical coupling reaction of a (cyclo)silane with one mole equivalent of dopant group precursor. Such products in which q=2 will generally be more likely to form the greater the value of n, but it is expected that the steric crowding of successive dopant groups will inhibit or prevent further substitution beyond a certain point. As a result, the photochemical coupling embodiment may be used to make compounds of the formula $(A_nH_{y-q})(DR^1_2)_q$, where n and y are as defined above, and q may be from 1 to n when the starting silane is cyclic and from 1 to n+2 when the starting silane is not cyclic.

A Second Exemplary Method for Synthesizing Dopant Group-Substituted Cyclosilanes In certain aspects of the present method, the reacting step comprises reducing a cyclosilane of the formula $A_nH_y$ (where y is an even integer of from n to 2n+2, preferably from n to 2n) with an alkali metal. Cyclosilanes in which y is an even integer greater than n, but less than 2n (e.g., the compound of FIG. 2), may be prepared in accordance with the known methods described in paragraph [0039] above, but in which the molar percentages of $ARX_3$ and $AR_2X_2$ are selected such that the intended reaction product(s) have a desired ratio of $(AH)$ to $(AH_2)$ groups.

In this second embodiment, the alkali metal is generally one other than Li, and the reacting comprises reacting m mole equivalents of the alkali metal and the cyclosilane with the dopant group precursor to form a dopant group-substituted cyclosilane of the formula $(A_nH_z)_mDR^1_{3-m}$, where z=y−1. For example, the alkali metal may be selected from the group consisting of sodium, potassium, rubidium, cesium and alloys thereof. Preferably, the alkali metal is sodium or potassium. Consequently, this second embodiment of the heterosubstituted (cyclo)silane synthesis method will be sometimes referred to as the "Na/K" embodiment.

In the exemplary "Na/K" embodiment, the dopant group precursor has the formula $DR^1_{3-m}X_m$. Preferred dopant group precursors of the formula $DR^1_{3-m}X_m$ include boron halides (e.g., boron trichloride, boron tribromide), alkylboron dihalides (e.g., methylboron dichloride, ethylboron dichloride, t-butylboron dibromide, t-hexylboron dichloride, etc.), arylboron dihalides (e.g., phenylboron dichloride), dialkyl boron halides (e.g., dimethylboron chloride, dimethylboron bromide, diethylboron chloride, di-t-butylboron chloride), diarylboron halides (e.g., diphenylboron chloride, diphenylboron bromide), phosphorous halides (e.g., phosphorous trichloride, phosphorous tribromide), alkylphosphorous dihalides (e.g., methylphosphorous dichloride, methylphosphorous dibromide, ethylphosphorous dichloride, n- and/or t-butyl-phosphorous dichloride, etc.), arylphosphorous dihalides (e.g., phenylphosphorous dichloride), dialkylphosphorous halides (e.g., dimethylphosphorous chloride, diethylphosphorous chloride, di-t-butylphosphorous chloride), diaryl phosphorous halides (e.g., diphenylphosphorous chloride, diphenylphosphorous bromide), mixed alkyl-aryl phosphorous halides (e.g., methylphenyl-phosphorous chloride, t-butylphenylphosphorous chloride, etc.), and the arsenic and antimony halide analogs of such phosphorous halides. Naturally, the boranes may be in the form of dimers; e.g., $(R^1_2D[\mu-X])_2$. As a result, the formula $DR^1_{3-m}X_m$ also refers to and/or includes dimers of the formulas $(R^1_2D[\mu-X])_2$, $(R^1XD[\mu-X])_2$ and $(X_2D[\mu-X])_2$.

Reaction conditions for the reducing step of the "Na/K" embodiment are generally similar to those for alkali metal reductions of other silanes or of organic compounds. For example, one may suspend the alkali metal in a solvent that is not reduced by the alkali metal (see the solvents below). In various embodiments, the (cyclo)silane may be present in an amount providing a 1:1, 2:1 or 3:1 molar ratio of (cyclo)silane to later-added dopant group precursor (the exact molar ratio depending on the value of m in the dopant group precursor), and the alkali metal may be present in an amount providing a slight molar excess (e.g., 1% or more, 3% or more, or 5% or more) of alkali metal relative to (cyclo)silane.

The "Na/K" reduction is generally started at a relatively low initial temperature (e.g., from −78° C. to ambient temperatures [e.g., from about 15° C. to about 30° C.]), from about −60° C. to about 0° C., or from about −40° C. to about −5° C.). The reaction vessel and/or the radiation source may be conventionally cooled using a water jacket (which may use recirculating ice water or a subzero aqueous salt solution), dry ice bath, or other conventional reaction cooling means. The reducing reaction may be conducted at this temperature for a length of time of from 5 minutes to 16 hours, 15 minutes to 8 hours, or 30 minutes to 4 hours, depending on the scale of the reaction and/or the concentration(s) of the reactant(s). Optionally, the reduction reaction mixture may be warmed to a target temperature higher than the initial temperature (e.g., from about −20° C. to the reflux temperature of the solvent, from about 0° C. to about 50° C., or about ambient temperatures) for a length of time of from 30 minutes to 16 hours, 1 hours to 12 hours, or 2 to 8 hours, depending on the scale of the reaction and/or the concentration(s) of the reactant(s). Generally, the higher the temperature, the shorter the reaction time. The reaction vessel will generally be purged by repeated vacuum/inert gas addition cycles to place the reaction under a substantially inert atmosphere.

The solvent may be any relatively non-polar, non-reactive solvent used in alkali metal reductions. Preferably, the solvent comprises or consists essentially of one or more alkanes (e.g., a $C_5$-$C_{12}$ or $C_6$-$C_{10}$ alkane), cycloalkanes (e.g., a $C_5$-$C_{10}$ cycloalkane), arenes (e.g., benzene), substituted arenes (e.g., toluene, xylenes, etc.), aliphatic ethers (e.g., di-$C_2$-$C_6$ alkyl ethers, methyl $C_4$-$C_6$ alkyl ethers and di-$C_1$-$C_4$ alkyl $C_2$-$C_6$ alkylene diethers [e.g., glyme]), and/or cyclic ethers (such as tetrahydrofuran and dioxane).

The "coupling" reaction in the "Na/K" embodiment may comprise adding the dopant group precursor of the formula $DR^1{}_{3-m}X_m$ to the reduced (cyclo)silane (e.g., dropwise by syringe, in a solution by addition funnel, via a double-ended needle, etc.) at a temperature of from −78° C. to the reflux temperature of the solvent, from about −40° C. to about 50° C. (or the solvent reflux temperature, whichever is lower), or from about 0° C. to ambient temperatures, for a length of time of from 15 minutes to 16 hours, 30 minutes to 12 hours, or 1 hour to 8 hours, depending on the scale of the reaction and/or the concentration(s) of the reactant(s). Optionally, the coupling reaction mixture may be warmed to a target temperature higher than the initial temperature (e.g., from about 0° C. to the reflux temperature of the solvent, or from ambient temperatures to about 50° C.) for a length of time of from 30 minutes to 16 hours, 1 hours to 12 hours, or 2 to 8 hours, depending on the scale of the reaction and/or the concentration(s) of the reactant(s). Generally, a slight molar excess (e.g., 1% or more, 2% or more, or 3% or more) of dopant group precursor (calculated on the number of halogen atoms) relative to alkali metal is added.

When m=1, about one mole equivalent of dopant group precursor is added to the reduced (cyclo)silane to form a dopant group-substituted (cyclo)silane of the formula $(A_nH_z)DR^1{}_2$. When m=2, about one-half mole equivalent of dopant group precursor is added to the reduced (cyclo)silane to form a dopant group-substituted (cyclo)silane of the formula $(A_nH_z)_2DR^1$. When m=3, about one-third mole equivalent of dopant group precursor is added to the reduced (cyclo)silane to form a dopant group-substituted (cyclo)silane of the formula $D(A_nH_z)_3$.

A Third Exemplary Method for Synthesizing Dopant Group-Substituted (Cyclo)silanes In a third exemplary embodiment of the present method of synthesizing dopant group-substituted silanes similar to the second exemplary embodiment above, the alkali metal is Li, the dopant group precursor has the formula $DR^1{}_2X$, and the reacting step comprises reacting two mole equivalents of the alkali metal and the dopant group precursor with the cyclosilane to form a dopant group-substituted silane of the formula $R^1{}_2D$-$(A_nH_y)$-$DR^1{}_2$. This embodiment of the present method for synthesizing hetero-substituted silanes (and, as will be discussed below, heterocyclosilanes) may therefore be known as the "Li" embodiment.

However, in an alternative "Li" embodiment, the dopant group precursor has the formula $DR^1X_2$, and this aspect of the invention provides a method of making a heterocyclosilane. This method generally comprises the steps of (a) reducing a cyclosilane of the formula $A_nH_y$ with at least two mole equivalents of lithium, where n is an integer from 3 to 12, y is from n to 2n, and each of the n instances of A is independently Si or Ge; and (b) reacting the reduced (cyclo)silane with a dopant group precursor of the formula $DR^1X_2$ to form a heterocyclosilane compound, where D is Sb, As, P or B, and $R^1$ is independently alkyl, aryl, aralkyl, or $AR^2{}_3$ (where $R^2$ is hydrogen, alkyl, aryl, aralkyl, or $A_pH_{2p+1}$, 1≤p≤4), and each instance of X is independently a halogen. This alternative "Li" embodiment may further comprise (c) purifying and/or isolating the heterocyclosilane compound.

Generally, the reaction conditions (e.g., solvent, molar reactant ratios, temperature, length of reaction time, etc.) for each of the reduction and coupling reactions in this third exemplary method are the same as for the second exemplary method described above. Only the formulas of the starting materials typically differ, although conditions may depend to some extent on the selection of certain (cyclo)silanes and dopant group precursors. For example, ring-strained cyclosilanes (e.g., the compound of FIG. 2, having two four-membered rings) may be reduced at a lower temperature and/or for a shorter period of time than less ring-strained cyclosilanes (e.g., cyclopentasilane, c-$[SiH_2]_5$). Also, sterically hindered dopant group precursors (e.g., di-t-butylphosphorous chloride, $[(CH_3)_3C]_2P$—Cl) may benefit more from higher coupling reaction temperatures and/or longer coupling reaction times than less hindered dopant group precursors (e.g., dimethylphosphorous chloride, $[CH_3]_2P$—Cl).

In one example, cyclopentasilane may be reduced with two mole equivalents of Li metal (suspended in dry THF at about 0° C. under an inert atmosphere, then warmed to room temperature for about 12-16 hours after the addition of cyclopentasilane), then two mole equivalents of di-t-butylphosphorous chloride (dissolved in dry THF) may be added to the reaction mixture at about 0° C. by addition funnel under an inert atmosphere. Thereafter, the coupling reaction mixture may be refluxed for 4-8 hours to provide $([CH_3]_3C)_2P$—$(SiH_2)_5$—$P(C[CH_3]_3)_2)$, the compound of FIG. 1H in which $R^1$=t-butyl, —$C(CH_3)_3$, after isolation and/or purification using conventional techniques (e.g., filtering to remove insoluble solid-phase by-products, evaporating most if not all of the solvent by vacuum, precipitating certain impurities by addition of a non-polar solvent such as toluene or [cyclo]hexane, then [re]crystallizing the final product, optionally after evaporating some of the non-polar solvent). A similar process can be performed with c-$(SiH)_{10}$ to form the compound of FIG. 1I in which $R^1$=t-butyl.

Figure 3:
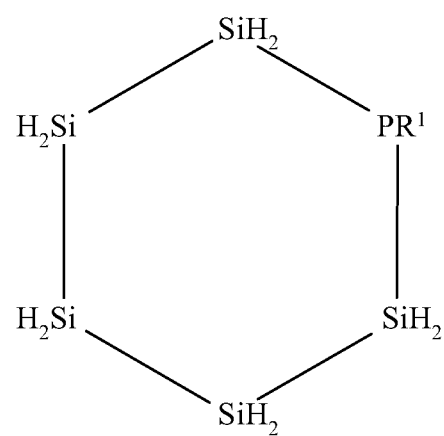
FIG. 3 shows a representative heterocyclosilane synthesized in accordance with one embodiment of the present invention.

Alternatively, after reducing cyclopentasilane with two mole equivalents of Li metal as described in the preceding paragraph, one mole equivalent of t-butylphosphorous dichloride may be added to the reaction mixture and isolated and/or purified as described above to provide c-$(SiH_2)_5P$—$C(CH_3)_3$, the compound of FIG. 3 in which $R^1$=t-butyl, —$C(CH_3)_3$.

Exemplary Isolation and/or Purification Steps

The present method may further comprise the step of purifying and/or isolating the hetero-substituted (cyclo)silane (or heterocyclosilane). Such purifying and/or isolating typically comprises removing solid by-product(s) from the reaction mixture by filtration. Alternatively, the reaction mixture can be passed through a column of silica or acidic aluminum gel to remove solid by-product. The isolating and/or purifying may further comprise removing the remainder of the solvent. Alternatively, isolating and/or purifying may comprise distilling the hetero-substituted (cyclo)silane (or heterocyclosilane), optionally under reduced pressure (e.g., from 0.1 to 50 Torr) and/or at ambient temperature or higher (e.g., from about 15° C. to about 90° C., or from about 20° C. to about 60° C.).

CONCLUSION/SUMMARY

Thus, the present invention provides compounds of the formula $(A_nH_z)_m(DR^1{}_{3-m})_q$, compositions (e.g., ink formulations) containing such compounds, and methods of synthesizing such compounds and making such compositions. In the present compounds, n is from 3 to 12, m is n is an integer from 3 to 12, z is from (n−q) to (2n+2−q), m is an integer from 1 to 3, each of the n instances of A is independently Si or Ge, D is Sb, As, P or B, q is generally 1 or 2, and each of the (3−m) instances of $R^1$ is independently H, alkyl, aryl, aralkyl, or $AR^2_3$ (where $R^2$ is hydrogen, alkyl, aryl, aralkyl, or $A_pH_{2p+1}$, p being an integer of 1 to 4); such that none of the covalent A-D bonds in the present compound is in a cyclic ring, and when m=1 and $A_nH_z$ is a linear or branched (acyclic) group of the formula n-$A_nH_{2n°2−q}$, then at most one of the (3−m) instances of $R^1$ is H. The compounds and compositions are generally useful for making (e.g., by printing or spin-coating, then curing and/or annealing) doped semiconductor thin films. Thus, the present invention advantageously provides a means for obtaining commercial qualities and quantities of thin doped semiconductor films from a "doped liquid silicon" composition.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A method of making a dopant group-substituted (cyclo)silane, comprising:
   reacting a (cyclo)silane of the formula $A_nH_y$ with an alkali metal and a dopant group precursor of the formula $DR^1_3$ or $DR^1_{3-m}X_m$ to form a dopant group-substituted (cyclo)silane compound, where n is an integer from 3 to 12, y is an even integer of from n to 2n+2, in is an integer from 1 to 3, each of the n instances of A is independently Si or Ge, D is Sb, As, P or B, each of the (3−m) instances of $R^1$ is independently H, alkyl, aryl, aralkyl, or $AR^2_3$ (where $R^2$ is hydrogen, alkyl, aryl, aralkyl, or $A_pH_{2p+1}$, 1≤p≤4), and each of the instances of X is independently a halogen; and
   b) purifying and/or isolating the dopant group-substituted (cyclo)silane compound.

2. The method of claim 1, wherein reacting said (cyclo)silane with said alkali metal and said dopant group precursor comprises reducing said (cyclo)silane of the formula $A_nH_y$ with said alkali metal.

3. The method of claim 2, wherein said dopant group precursor has the formula $DR^1_{3-m}$.

4. The method of claim 3, wherein said (cyclo)silane of the formula $A_nH_y$, comprises a cyclosilane in which y is an even integer of from n to 2n, said alkali metal comprises Li, said dopant group precursor has the formula $DR^1_2X$, and said reacting comprises reacting two mole equivalents of said alkali metal and said dopant group precursor with said cyclosilane to form a dopant group-substituted silane of the formula $R^1_2D-(A_nH_y)-DR^1_2$.

5. The method of claim 3, wherein said alkali metal does not comprise Li, and said reacting comprises reacting m mole equivalents of said alkali metal and said (cyclo)silane with one mole equivalent of said dopant group precursor to form a dopant group-substituted cyclosilane of the formula $(A_nH_z)_mDR^1_{3-m}$, where z=y−1.

6. The method of claim 5, wherein m is 1.

7. The method of claim 5, wherein said alkali metal comprises a member selected from the group consisting of sodium, potassium, rubidium, cesium and alloys thereof.

8. The method of claim 1, wherein A is Si.

9. The method of claim 1, wherein each $R^1$ is independently H or a $C_1$-$C_6$ alkyl, $C_6$-$C_{12}$ aryl, $SiH_3$, or $Si(SiH_3)_3$, group.

10. The method of claim 1, wherein m is 1.

11. The method of claim 1, wherein D is P or B.

12. The method of claim 1, further comprising mixing said (cyclo)silane and said dopant precursor compound in a solvent prior to reacting said (cyclo)silane with said alkali metal and said dopant group precursor, and said purifying and/or isolating comprises removing most of said solvent.

13. A method of making a heterocyclosilane, comprising the steps of:
   a) reducing a cyclosilane of the formula $A_nH_y$ with at least two mole equivalents of lithium, where n is an integer from 3 to 12, y is an even integer of from n to 2n, and each of the n instances of A is independently Si or Ge; and
   b) reacting said reduced cyclosilane with a dopant group precursor of the formula $DR^1X_2$ to form a heterocyclosilane compound, where D is Sb, As, P or B, and $R^1$ is independently alkyl, aryl, aralkyl, or $AR^2_3$ (where $R^2$ is hydrogen, alkyl, aryl, aralkyl, or $A_pH_{2p+1}$, 1≤p≤4), and each instance of X is independently a halogen.

14. The method of claim 13, wherein said cyclosilane has the formula $A_nH_{2n}$.

15. The method of claim 13, wherein said heterocyclosilane compound has the formula $A_nH_yDR^1$.

16. The method of claim 13, further comprising purifying and/or isolating the heterocyclosilane compound.

17. The method of claim 2, wherein said (cyclo)silane of the formula $A_nH_y$ is reduced with said alkali metal before reacting with said dopant group precursor.

18. A method of making a dopant group-substituted (cyclo)silane, comprising:
   a) reacting a (cyclo)silane of the formula $A_nH_y$ with a dopant group precursor of the formula $DR^1_3$ or $DR^1_{3-m}X_m$ to form a dopant group-substituted (cyclo)silane compound, where n is an integer from 3 to 12, y is an even integer of from n to 2n+2, m is an integer from 1 to 3, each of the n instances of A is independently Si or Ge, D is Sb, As, P or B, each of the (3−m) instances of $R^1$ is independently a $C_1$-$C_6$ alkyl, $C_6$-$C_{12}$ aryl, $SiH_3$, or $Si(SiH_3)_3$ group, and each of the instances of X is independently a halogen; and
   b) purifying and/or isolating the dopant group-substituted (cyclo)silane compound.

19. The method of claim 18, further comprising reacting said (cyclo)silane of the formula $A_nH_y$ with an alkali metal before reacting with said dopant group precursor.

20. The method of claim 18, wherein $R^1$ is t-butyl, phenyl, $SiH_3$ or $Si(SiH_3)_3$.

* * * * *